United States Patent [19]

Wagstaff

[11] 4,291,188

[45] Sep. 22, 1981

[54] PROCESS FOR THE PREPARATION OF METHANE AND/OR ETHANE

[75] Inventor: Nigel Wagstaff, Amsterdam, Netherlands

[73] Assignee: Shell Oil Company, Houston, Tex.

[21] Appl. No.: 129,445

[22] Filed: Mar. 11, 1980

[30] Foreign Application Priority Data

Mar. 14, 1979 [NL] Netherlands .......................... 7902021

[51] Int. Cl.$^3$ ................................................ C07C 4/02
[52] U.S. Cl. ...................................... 585/752; 208/120
[58] Field of Search .......................... 585/752; 208/120

[56] References Cited

U.S. PATENT DOCUMENTS

| | | | |
|---|---|---|---|
| 3,941,871 | 3/1976 | Dwyer et al. | 423/331 |
| 4,061,724 | 12/1977 | Grose et al. | 423/339 |
| 4,073,865 | 2/1978 | Flanigen et al. | 423/335 |
| 4,148,713 | 4/1979 | Rollmann | 208/120 |

*Primary Examiner*—Curtis R. Davis
*Attorney, Agent, or Firm*—Ronald R. Reper

[57] ABSTRACT

A process for the production of methane and ethane from a $C_2$–$C_4$ paraffins hydrocarbon feed stream of higher average carbon number than the product which comprises contacting said feed with certain crystalline silicates at an elevated temperature and a pressure above 10 bar.

9 Claims, No Drawings

PROCESS FOR THE PREPARATION OF METHANE AND/OR ETHANE

BACKGROUND OF THE INVENTION

The invention relates to a process for the preparation of methane and/or ethane from a paraffin with 2-4 carbon atoms in the molecule or from a hydrocarbon mixture which consists of more than 75% w $C_{2-4}$ paraffins and which $C_{2-4}$ paraffins have an average molar carbon number which is at least 0.5 higher than that of the $C_2^-$ paraffin fraction of the product, using a certain crystalline silicate as the catalyst.

In an investigation by the Applicant concerning the above-mentioned process it has been found that the methane + ethane weight percentage in the product is in the first place greatly dependent on the value of y in the formula which gives the overall composition of the silicate, and further on the pressure used in the process. It was found that to prepare a product whose methane + ethane weight percentage is acceptable for commercial use of the process, y should be at least 0.005 and the process should be carried out at a pressure above 10 bar.

SUMMARY OF THE INVENTION

The present invention therefore relates to a process for the preparation of methane and/or ethane, in which a $C_{2-4}$ paraffin or a hydrocarbon mixture which consists of more than 75% w $C_{2-4}$ paraffins and which $C_{2-4}$ paraffins have an average molar carbon number which is at least 0.5 higher than that of the $C_2^-$ paraffin fraction of the product, is contacted at a pressure of above 10 bar and a crystalline silicate as defined below, in which in the formula which gives the overall composition of the silicate, the value of y is at least 0.005.

DESCRIPTION OF PREFERRED EMBODIMENTS

In the process according to the invention the starting material should be a $C_{2-4}$ paraffin or a hydrocarbon mixture which consists of more than 75% w $C_{2-4}$ paraffins. Suitable $C_{2-4}$ paraffins are ethane, propane, butane and isobutane. If the starting material is a hydrocarbon mixture which comprises in addition to one or more $C_{2-4}$ paraffins one or more other hydrocarbons, these other hydrocarbons may be, inter alia, monoolefins, diolefins, methane or $C_5^+$ paraffins. As regards the $C_{2-4}$ paraffins which are present in the feed, they should have an average molar carbon number which is at least 0.5 higher than that of the $C_2^-$ paraffin fraction of the product. In this connection the average molar carbon number should be taken to mean:

$$\frac{\Sigma N \times \text{NUMBER OF MOLES OF } C_n \text{ PARAFFIN}}{\Sigma \text{ number of moles of } C_n \text{ paraffin}}$$

For the feed n may be 2 and/or 3 and/or 4 and for the product n may be 1 and/or 2. Therefore, the average molar carbon number for the $C_{2-4}$ paraffins in the feed may vary between 2 and 4 ($N_F$) and for the $C_2^-$ paraffin fraction of the product between 1 and 2 ($N_p$). In the process according to the invention the requirement: $N_F \geq N_p + 0.5$ should be satisfied. A very suitable feed for the present process is a hydrocarbon mixture consisting substantially of $C_3$ and $C_4$ paraffins which has been obtained as a by-product in mineral oil production.

The process according to the invention is preferably carried out at a temperature of from about 400° to about 800° C. and particularly of from 425° to 650° C., a pressure below 100 bar and particularly from 15 to 75 bar and a space velocity of from 0.1 to 20 $g.g^{-1}.h^{-1}$ and particularly from 0.5 to 10 $g.g^{-1}.h^-$. If desired, the process may be carried out in the presence in hydrogen.

Depending on the temperature used, the process according to the invention can yield a product whose $C_2^-$ paraffin fraction substantially consists either of methane, or of ethane. Temperatures of from 425° to 500° C. give a product whose $C_2^-$ paraffin fraction consists substantially of ethane, whereas at temperatures of from 530° to 650° C. a product is obtained whose $C_2^-$ paraffin fraction consists substantially of methane.

In the process according to the invention a $C_{2-4}$ paraffin or a hydrocarbon mixture which consists of more than 75% w $C_{2-4}$ paraffins is converted into methane and/or ethane by contacting this feed with certain crystalline silicates. The said crystalline silicates are characterized in that after 1 hour's calcining in air they have the following compositions:

(a) thermally stable up to a temperature above 600° C., (b) an X-ray powder diffraction pattern showing, inter alia, the reflections given in Table A.

TABLE A

| Radiation : Cu-K 2 $\theta$ | Wavelength 0.15418 nm relative intensity |
| --- | --- |
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 23.1–23.4 | VS |
| 23.8–24.1 | VS |
| 24.2–24.8 | S |
| 29.7–30.1 | M | wherein the letters used have the following meanings:

VS = very strong; S = strong; M = moderate; W = weak;

$\theta$ = angle according to Bragg, (c) after conversion of the silicate into the H-form and after evacuation at $2 \times 10^{-9}$ bar and 400° C. for 16 hours and measured at a hydrocarbon pressure of $8 \times 10^{-2}$ bar and 100° C. the adsorption of n-hexane is at least 0.8 mmol/g, the adsorption of 2,2-dimethylbutane at least 0.5 mmol/g and the ratio $$\frac{\text{adsorption of n-hexane}}{\text{adsorption of 2,2-dimethylbutane}} \text{ at least 1.5,}$$

(d) the composition, expressed in moles of the oxides, is as follows:

$y.(1.0 + 0.3)M_{n/2}O.y.Al_2O_3.SiO_2$, wherein M = H and/or alkali metal and/or alkaline-earth metal, n is the valency of M and $0 < y \leq 0.1$.

For the adsorption measurements mentioned under (c) the silicate should first be converted into the H-form. This conversion is effected by boiling the silicate calcined at 500° C. with 1.0 molar $NH_4NO_3$ solution, washing with water, boiling again with 1.0 molar $NH_4NO_3$ solution and washing, drying at 120° C. and calcining at 500° C. The complete X-ray powder diffraction pattern of a typical example of a silicate suitable for use according to the invention is shown in Table B (radiation: Cu-K; wavelength: 0.15418 nm).

TABLE B

| $2\theta$ | relative intensity (100 $I:I_o$) | description |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100* | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

*$I_o$ = intensity of the strongest separate reflection present in the pattern.

The letters used in Table B for describing the reflections have the following meanings:
SP=sharp; SR=shoulder; NL=normal; BD=broad; $\theta$=angle according to Bragg.

The crystalline silicates which are used as the catalyst in the process according to the invention can be prepared starting from an aqueous mixture containing the following compounds: one or more compounds of an alkali or alkaline-earth metal (M), one or more compounds containing an organic cation (R) or from which such a cation is formed during the preparation of the silicate, one or more silicon compounds and one or more aluminum compounds. Exemplary organic cations include, e.g., primary, secondary, and tertiary amines and quaternary ammonium hydroxide. The preparation is performed by maintaining the mixture at elevated temperature until the silicate has been formed and subsequently separating the crystals of the silicate from the mother liquor. In the aqueous mixture from which the silicates are prepared the various compounds should be present in the following ratios, expressed in moles of the oxides:

$M_{2/n}O:(R)_{2/p}O = 0.1–20$,
$(R)_{2/p}O:SiO_2 = 0.01–0.5$,
$SiO_2:Al_2O_3 < 400$, and
$H_2O:SiO_2 = 5–50$;

n is the valency of M and p is the valency of R.

In the preparation of the silicates it is preferred to start from a base mixture in which M is present in a sodium compound and R in a tetrapropylammonium compound.

For the silicates which are suitable for use as the catalyst $y \geqq 0.005$. Preference is given to the use of silicates with $y \geqq 0.01$.

The value of y in the formula which gives the composition of the silicates can be controlled with the aid of the molar ratio of $SiO_2$ to $Al_2O_3$ in the starting mixture, in the sense that silicates with a lower value for y are obtained according as the molar ratio of $SiO_2$ to $Al_2O_3$ in the starting mixture is chosen higher.

The silicates prepared as described above contain alkali metal ions and/or alkaline-earth metal ions and organic cations. When suitable exchange methods are used, the alkali metal ions and alkaline-earth metal ions can be replaced by other cations, such as hydrogen ions or ammonium ions. Organic cations can very conveniently be converted into hydrogen ions by calcining the silicates. The crystalline silicates which are used as the catalyst in the process according to the invention preferably have an alkali metal content of less than 0.1% w, and particularly less than 0.01% w. When the crystalline silicates are used as the catalyst, they may, if desired, be combined with a natural or synthetic binder material such as bentonite or kaolin.

Although the silicates that are used in the process according to the invention do have a high catalytic activity as such, it may, in addition, be recommendable to incorporate one or more catalytically active metal components. Very suitable catalytically active metal components are zinc and noble metals of group VIII. When a noble metal of group VIII is used, platinum, palladium or iridium is preferably chosen, and in particular platinum. Very favorable results can be obtained in the process according to the invention when a silicate is used that contains zinc, or platinum, or a combination of zinc and platinum. A silicate that is preferably used in the process according to the invention is one that contains 0.05 to 20% w and particularly 0.1 to 10% w zinc and/or 0.1 to 5% w and particularly 0.1 to 2% w of a noble metal of group VIII. If in the process according to the invention use is made of a silicate which contains one or more catalytically active metal components, preference is given to a silicate in which incorporation of the catalytically active metal components has been performed by impregnating the silicate with an aqueous solution of one or more salts of the metals concerned, followed by drying and calcining of the impregnated material. When zinc is present in the catalyst preferably it is present in the form of the oxide.

The process according to the invention can very suitably be carried out by conducting the feed in upward and downward direction through a vertically mounted reactor, in which a fixed or moving bed of the catalyst concerned is present.

As was mentioned earlier, the process according to the invention can yield a product whose $C_2^-$ paraffin fraction substantially consists either of methane or of ethane, depending on the temperature used. The methane prepared according to the invention can be used very suitably as fuel gas to replace natural gas, while the ethane prepared according to the invention is very suitable for use as the feed for a thermal cracking unit for the preparation of ethylene.

The invention will now be explained with reference to the following example.

EXAMPLE

Three crystalline silicates (silicates A-C) were prepared by heating mixtures of $SiO_2$, $NaAlO_2$, NaOH and $[(C_3H_7)_4N]OH$ in water in an autoclave under autogenous pressure for 24 hours at 150° C. After the reaction mixture had cooled down, the silicates formed were filtered off, washed with water until the pH of the wash water was about 8 and dired for two hours at 120° C. After 1 hour's calcining in air at 500° C. the silicates A-C had the following properties:

(a) thermally stable up to a temperature above 800° C.

(b) an X-ray powder diffraction pattern substantially equal to the one given in Table B.

(c) after conversion of the silicate into the H-form and after evacuation at $2\times10^{-9}$ bar and 400° C. for 16 hours and measured at a hydrocarbon pressure of $8\times10^{-2}$ bar and 100° C., the adsorption of n-hexane is 1.2 mmol/g, the adsorption of 2,2-dimethylbutane 0.7 mmol/g and the ratio $$\frac{\text{adsorption of n-hexane}}{\text{adsorption of 2,3-dimethylbutane}} = 1.7,$$

(d) the composition expressed in moles of the oxides is the following:
silicate A: 0.030 $M_2O$. 0.030 $Al_2O_3.SiO_2$
silicate B: 0.0038 $M_2O$. 0.00 38 $Al_2O_3.SiO_2$
silicate C: 0.0059 $M_2O$. 0.0059 $Al_2O_3.SiO_2$
wherein M=H and Na.

The molar composition of the aqueous mixtures from which the silicates A-C were prepared are given in Table C.

TABLE C

| Silicate | A | B | C |
|---|---|---|---|
| $Na_2O$ | 1.5 | 16 | 8 |
| $Al_2O_3$ | 1 | 1 | 1 |
| $[(C_3H_7)_4N]_2O$ | 6.75 | 72 | 12 |
| $SiO_2$ | 37.5 | 400 | 200 |
| $H_2O$ | 675 | 7200 | 3600 |

The silicates I-III were prepared from the silicates A-C, respectively, by boiling the materials calcined at 500° C. with 1.0 molar $NH_4NO_3$ solution, washing with water, boiling again with 1.0 molar $NH_4NO_3$ solution and washing, drying at 120° C. and calcining at 500° C.

From the silicates I-III as the starting materials the silicates 1-6 were prepared, which contained zinc and-/or platinum. The preparation was effected by impregnating samples of the silicates I-III with an aqueous solution of one or more salts of the elements concerned, followed by drying and calcining of the impregnated material.

The silicates 1-6 had the following compositions:
Silicate 1: 1% w Pt on silicate I
Silicate 2: 2% w Zn on silicate I
Silicate 3: 10% w Zn on silicate I
Silicate 4: 0.33% w Pt+0.33% w Zn on silicate II
Silicate 5: 0.40% w Pt on silicate II
Silicate 6: 2% Zn on silicate II The silicates 1-6 and silicate I were tested as catalyst for the preparation of methane and ethane from propane or isobutane. The test was carried out in a 50-ml reactor containing a 5-ml fixed catalyst bed of the silicate concerned. Propane or isobutane was conducted over the catalyst at a temperature of from 475° and 580° C., a pressure of from 1.5 to 50 bar and a space velocity of 2 $g.g^{-1}.h^{-1}$. The results of these experiments are given in Table D. The following data are included in the table:

(a) the amount of methane in the product,
(b) the amount of ethane in the product,
(c) the total amount of methane and ethane in the product, and
(d) the temperature, pressure and feed used.

TABLE D

| Exp. No. | Silicate No. | Feed | Temp. °C. | Pressure, bar | Amount of $CH_4$ in Product, % w | Amount of $C_2H_6$ in Product, % w | Amount of $CH_4 + C_2H_6$ in Product, % w |
|---|---|---|---|---|---|---|---|
| 1 | 1 | propane | 475 | 15 | 14 | 59 | 73 |
| 2 | 1 | propane | 475 | 50 | 17 | 57 | 74 |
| 3* | 1 | propane | 475 | 50 | 20 | 58 | 78 |
| 4 | 1 | isobutane | 450 | 50 | 8 | 60 | 68 |
| 5 | 1 | isobutane | 550 | 50 | 42 | 22 | 64 |
| 6 | 1 | isobutane | 580 | 50 | 61 | 7 | 68 |
| 7 | 2 | propane | 475 | 30 | 19 | 35 | 54 |
| 8 | 3 | propane | 500 | 30 | 30 | 42 | 72 |
| 9 | 3 | propane | 520 | 30 | 33 | 38 | 71 |
| 10 | 3 | propane | 550 | 30 | 38 | 30 | 68 |
| 11 | 1 | propane | 475 | 15 | 19 | 35 | 54 |
| 12 | 2 | propane | 475 | 6 | 5 | 10 | 15 |
| 13 | 4 | propane | 475 | 15 | 6 | 22 | 28 |
| 14 | 4 | propane | 500 | 30 | 13 | 24 | 37 |
| 15 | 5 | propane | 475 | 15 | 5 | 22 | 27 |
| 16 | 5 | propane | 500 | 15 | 9 | 25 | 34 |
| 17 | 6 | propane | 550 | 1.5 | 6 | 9 | 15 |
| 18 | I | propane | 475 | 6 | 14 | 24 | 38 |

*Experiment 3 was carried out in the presence of hydrogen using a $H_2$/propane molar ratio of 1:4

Of the experiments shown in Table D only the numbers 1-11 are experiments according to the invention. These experiments were carried out at a pressure above 10 bar using as the catalyst a silicate which had the required y. In these experiments a product was obtained which consisted of a high percentage by weight of methane and ethane. The experiments 12-18 are outside the scope of the invention and have been included for comparison. In experiments 12-16 a silicate with too low y-value was used and in experiments 17 and 18 too low a pressure was used, which resulted in all cases in a product which consisted of an unacceptably low percentage by weight of methane and ethane.

What is claimed is

1. A process for the preparation of methane and/or ethane, which comprises contacting as feed a $C_{2-4}$ paraffin or a hydrocarbon mixture which consists of more than 75% $C_{2-4}$ paraffins and which $C_{2-4}$ paraffins have an average molar carbon number which is at least 0.5 higher than that of the $C_2-$ paraffin fraction of the product, at an elevated temperature of from 400° to 800° C., a pressure of above 10 to below 100 bar, and a space velocity of from 0.1 to 20 $g.g^{-1}.h^{-1}$ in a contact zone with a crystalline silicate as the catalyst, which silicate is characterized in that after 1 hour's calcining in air at 500° C. it has the following properties:

(a) thermally stable up to a temperature above 600° C.,
(b) an X-ray powder diffraction pattern showing, inter alia, the reflections give in Table A.

TABLE A

| Radiation : Cu—K 2θ | Wavelength 0.15418 nm relative intensity |
| --- | --- |
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings: VS=very strong; S=strong; M=moderate; W=weak; θ=angle according to Bragg.

(c) after conversion of the silicate into the H-form and after evacuation at $2 \times 10^{-9}$ bar and 400° C. for 16 hours and measured at a hydrocarbon pressure of $8 \times 10^{-2}$ bar and 100° C. the adsorption of n-hexane is at least 0.8 mmol/g, the adsorption of 2,2-dimethylbutane at least 0.5 mmol/g and the ratio $$\frac{\text{adsorption of n-hexane}}{\text{adsorption of 2,2-dimethylbutane}} \text{ at least 1.5,}$$

(d) the composition, expressed in moles of the oxides, is as follows:
y.(1.0±0.3)$M_{n/2}$O.y.$Al_2O_3$.$SiO_2$
wherein M=H and/or alkali metal and/or alkaline-earth metal, n is the valency of M and y≧0.01; and withdrawing a methane and ethane containing product from said catalyst zone.

2. A process according to claim 1 wherein said feed is a hydrocarbon mixture consisting substantially of $C_3$ and $C_4$ paraffins.

3. A process according to claim 1 wherein said contacting is carried out at a temperature of from 425° to 650° C., a pressure of from 15 to 75 bar and a space velocity of from 0.5 to 10 g.$g^{-1}$.$h^{-}$.

4. A process according to claim 3 wherein for the preparation of a product whose $C_2^-$paraffin fraction consists substantially of methane, said contacting is carried out at a temperature of from 530° to 650° C.

5. A process according to claim 3 wherein for the preparation of a product whose $C_2^-$paraffin fraction consists substantially of ethane, said contacting is carried out at a temperature of from 425° to 500° C.

6. A process according to claim 1 wherein said silicate has an alkali metal content less than 0.1% w.

7. A process according to claim 1 wherein said silicate also contains 0.05 to 20% w zinc and/or 0.01 to 5%w of a noble metal or group VIII.

8. A process according to claim 7 wherein said silicate contains 0.1 to 10% w zinc and/or 0.1 to 2% w of a noble metal of group VIII.

9. A process according to claim 8 wherein the noble metal of group VIII is selected from platinum, palladium and iridium, and mixtures thereof.

* * * * *